United States Patent
Franzen et al.

(10) Patent No.: US 8,674,146 B2
(45) Date of Patent: Mar. 18, 2014

(54) METHOD FOR PRODUCING ALKYLENE OXIDE ADDITION PRODUCTS

(75) Inventors: Stefan Franzen, Kamen (DE); Franz Büttgen, Hilden (DE); Ingomar Mrozek, Düsseldorf (DE); Bernhard Gutsche, Hilden (DE)

(73) Assignee: Cognis IP Management GmbH, Duesseldorf (DE)

( * ) Notice: Subject to any disclaimer, the term of this patent is extended or adjusted under 35 U.S.C. 154(b) by 382 days.

(21) Appl. No.: 12/440,461

(22) PCT Filed: Aug. 29, 2007

(86) PCT No.: PCT/EP2007/007530
§ 371 (c)(1),
(2), (4) Date: Mar. 7, 2009

(87) PCT Pub. No.: WO2008/028586
PCT Pub. Date: Mar. 13, 2008

(65) Prior Publication Data
US 2010/0041923 A1    Feb. 18, 2010

(30) Foreign Application Priority Data
Sep. 7, 2006 (DE) .................. 10 2006 041 904

(51) Int. Cl.
C07C 41/02 (2006.01)
C07C 41/03 (2006.01)
B01J 8/00 (2006.01)

(52) U.S. Cl.
CPC .............. *C07C 41/02* (2013.01); *C07C 41/03* (2013.01)
USPC .................... 568/618; 568/620; 568/671

(58) Field of Classification Search
None
See application file for complete search history.

(56) References Cited

U.S. PATENT DOCUMENTS

| | | | |
|---|---|---|---|
| 4,750,941 A * | 6/1988 | Gerich | 134/22.12 |
| 5,026,923 A | 6/1991 | Kemp | |
| 5,723,094 A | 3/1998 | Sunavala | |
| 5,811,595 A | 9/1998 | Ellis | |
| 6,646,145 B1 * | 11/2003 | Behler et al. | 554/149 |
| 7,247,276 B2 * | 7/2007 | Schuppich et al. | 422/129 |
| 2005/0170142 A1 * | 8/2005 | Remy | 428/141 |
| 2005/0245628 A1 * | 11/2005 | Hubel et al. | 521/137 |

FOREIGN PATENT DOCUMENTS

| | | |
|---|---|---|
| DE | 10036601 | 2/2002 |
| DE | 10054462 | 6/2002 |
| EP | 0903174 | 3/1999 |
| EP | 1462446 | 9/2004 |
| EP | 1586372 | 10/2005 |
| WO | WO 00/51955 | 9/2000 |
| WO | WO 02/009866 | 2/2002 |
| WO | WO 2008/028586 | 3/2008 |

OTHER PUBLICATIONS

Dummann et al., The capillary-microreactor: a new reactor concept for the intensification of heat and mass transfer in liquid-liquid reactions, Catalysis Today, 2003, 79-80, pp. 433-439.*
Angell, J., et al., "Silicon Micromechanical Devices," *Scientific American*, 248:4, pp. 44-55 (Apr. 1983).
Burns, J. R., et al., "Development of a Microreactor for Chemical Production," *Trans IChemE*, vol. 77, part A, pp. 206-211 (1999).
Newsfront, Edited by Agnes Shanley, "Microreactors Find New Niches," *Chemical Engineering, Access Intelligence Association*, pp. 30-33 (Mar. 1997).
PCT/EP2007/007530 International Search Report dated Dec. 12, 2007.
Non-Final Office Action in U.S. Appl. No. 12/440,459, dated Sep. 1, 2011, 8 pgs.
Kestenbaum, Harry et al., "Silver-Catalyzed Oxidation of Ethylene to Ethylene Oxide in a Microreaction System", *Ind. Eng. Chem. Res*, *41* 2002, 710-719.

* cited by examiner

*Primary Examiner* — Rosalynd Keys
(74) *Attorney, Agent, or Firm* — Servilla Whitney LLC

(57) ABSTRACT

The invention relates to a method for producing alkylene oxide addition products by reaction of compounds having a nucleophilic center with alkylene oxides in a reactor having a large inner surface. The invention is characterized in that the reaction is carried out exclusively in the liquid phase.

17 Claims, No Drawings

METHOD FOR PRODUCING ALKYLENE OXIDE ADDITION PRODUCTS

CROSS REFERENCE TO RELATED APPLICATIONS

This application is the National Phase entry of PCT/EP2007/007530, filed Aug. 29, 2007, which claims priority to German patent application number DE 10 2006 041 904.9, filed Sep. 7, 2006, both of which are incorporated herein by reference in their entireties.

FIELD OF THE INVENTION

The invention is in the field of the nonionic surfactants and relates to an improved process for preparing alkylene oxide addition products in the liquid phase.

BACKGROUND OF THE INVENTION

Addition products of alkylene oxides onto alcohols, acids or amines are important industrial products which find frequent use especially as nonionic surfactants.

The alkoxylation is typically performed batchwise, for example in stirred autoclaves or loop reactors at temperatures between 80 and 130° C.; alternatively, the liquid reaction mixture can also be dispersed in an alkylene oxide-containing gas phase. On this subject, reference is made by way of example to a review article in Chem. Res. 25, 9482-9489 (2005). Typically, the compound with the nucleophilic center—for example an alcohol, a carboxylic acid, an ester or an amine—is initially charged together with the catalyst and then the desired amount of alkylene oxide is injected, which, depending on the temperature, generally establishes a pressure of up to 12 bar. Suitable catalysts are basic compounds, for example alkali metal alkoxides, or Lewis acids, the latter having the disadvantage that they tend to form considerable amounts of undesired polyglycol ethers. All these processes involve a liquid reaction mixture and an alkylene oxide-containing gas phase, which is afflicted in generic terms with the problem of insufficient mass transfer at the phases interface and therefore reduced conversion.

The safety problems which additionally arise as a result of alkylene oxides in the gas phase are described, for example, in DE 10054462 B4. The enrichment of ethylene oxide or propylene oxide in the gas phase causes the risk of decomposition. The concentration of the alkylene oxide is therefore kept low by inert gases. According to the teaching of this publication, the alkoxylation is performed in a tubular reactor which is configured as a plate heat exchanger. Alkylene oxide is fed in at several points in the reactor. The amount is selected precisely such that the solubility of the alkylene oxide in the liquid reaction mixture is not exceeded, in order to prevent the local formation of a gas phase.

In this context, reference is also made to the international patent application WO 02/009866 A1 (CPC). This document discloses a microreactor, for purposes including the alkoxylation of fatty alcohols, in which the reaction takes place between two or more essentially plane-parallel plates or layers, at least one of these plates or layers being a fluid conduction plate and being structured and/or arranged such that the fluid reactant flows only owing to the influence of gravity and/or to capillary forces within at least one essentially uninterrupted capillary thread along the surface or layer, and as it does so comes into contact with the gaseous reactant and reacts. However, this is nothing more than a miniaturized falling-film reactor in which the reaction takes place at the interface of liquid and gaseous phases, and which is therefore afflicted with the technical disadvantages already described above.

It was therefore an object of the present invention to provide an improved process for preparing alkylene oxide addition products, which enables more intense mass transfer and hence higher conversions, while also permitting higher alkylene oxide concentrations, without this being at the cost of reduced occupational safety.

DETAILED DESCRIPTION OF PREFERRED EMBODIMENTS

The invention provides a process for preparing alkylene oxide addition products by reacting compounds having a nucleophilic center with alkylene oxides in a reactor with high internal surface area, wherein the reaction is performed exclusively in the liquid phase.

It has been found that, surprisingly, the alkoxylation in the liquid phase using reactors with high internal surface area overcomes disadvantages known from the prior art, and now, more particularly, it is also possible to use higher alkylene oxide concentrations without this resulting in safety problems. At the same time, the problem of insufficient contact between vapor and liquid phases is avoided, and so the process also leads to higher conversions.

Compounds with Nucleophilic Molecule Groups

The selection of the reactant for the subsequent alkoxylation is uncritical per se. The only condition is that it is a compound with a nucleophilic center, preferably with an acidic hydrogen atom. Useful for this purpose are especially alcohols of the formula (I)

$$R^1OH \qquad (I)$$

in which $R^1$ is a linear or branched hydrocarbon radical having from 1 to 22 carbon atoms, preferably from 8 to 18 carbon atoms, and from 0 or 1 to 3 double bonds. Typical examples are, in addition to the lower aliphatic alcohols methanol, ethanol and the isomeric butanols and pentanols, the fatty alcohols, specifically caproic alcohol, capryl alcohol, 2-ethylhexyl alcohol, capric alcohol, lauryl alcohol, isotridecyl alcohol, myristyl alcohol, cetyl alcohol, palmoleyl alcohol, stearyl alcohol, isostearyl alcohol, oleyl alcohol, elaidyl alcohol, petroselinyl alcohol, linolyl alcohol, linolenyl alcohol, elaeostearyl alcohol, arachyl alcohol, gadoleyl alcohol, behenyl alcohol, erucyl alcohol and brassidyl alcohol, and technical-grade mixtures thereof, which are obtained, for example, in the high-pressure hydrogenation of technical-grade methyl esters based on fats and oils, or aldehydes from the Roelen oxo process, and as a monomer fraction in the dimerization of unsaturated fatty alcohols. Preference is given to technical-grade fatty alcohols having from 12 to 18 carbon atoms, for example coconut fatty alcohol, palm fatty alcohol, palm kernel fatty alcohol or tallow fatty alcohol.

A further group of compounds which are suitable as starting materials for the alkoxylation is formed by the carboxylic acids of the formula (II)

$$R^2CO-OH \qquad (II)$$

in which $R^2CO$ is a linear or branched acyl radical having from 1 to 22 carbon atoms and from 0 or 1 to 3 double bonds. Typical examples are in particular the fatty acids, specifically caproic acid, caprylic acid, 2-ethylhexanoic acid, capric acid, lauric acid, isotridecanoic acid, myristic acid, palmitic acid, palmoleic acid, stearic acid, isostearic acid, oleic acid, elidic acid, petrosilic acid, linoleic acid, linolenic acid, elaeostearic acid, arachic acid, gadoleic acid, behenic acid and erucic acid, and technical-grade mixtures thereof, which are obtained, for example, in the pressure cleavage of natural fats and oils, in the reduction of aldehydes from the Roelen oxo process, or the dimerization of unsaturated fatty acids. Preference is given to technical-grade fatty acids having from 12 to 18 carbon atoms, for example coconut fatty acid, palm fatty acid, palm kernel fatty acid or tallow fatty acid. It will be appreciated that it is also possible to alkoxylate functionalized carboxylic acids, for example hydroxycarboxylic acids such as ricinoleic acid or citric acid, or dicarboxylic acids such as adipic acid. Instead of the acids, it is also possible to use the corresponding esters with $C_1$-$C_{22}$ alcohols or glycerol; here, an insertion into the ester group then takes place.

Instead of the carboxylic acids, it is also possible to use esters thereof with alcohols having from 1 to 22 and preferably from 1 to 4 carbon atoms or polyols, especially glycerol, trimethylolpropane or pentaerythritol. In addition to the corresponding methyl carboxylates, the glyerides and among these in turn the partial glycerides are preferred. When they are full esters, the alkylene oxide groups are inserted into the carbonyl ester bond.

Finally, a further group of compounds suitable as starting materials is also that of amines of the formula (III)

$$R^3\text{—NH—}R^4 \qquad (III)$$

in which $R^3$ and $R^4$ are each independently hydrogen, alkyl groups having from 1 to 18 carbon atoms or hydroxyalkyl groups having from 1 to 4 carbon atoms. Typical examples are methylamine, dimethylamine, ethylamine, diethylamine, methylethylamine, and the different propyl, butyl, pentyl and fatty amines of analogous structure.

Structured Reactors and Micro Reaction Systems

The term "structured reactor" is understood to mean an array of reaction channels which can be operated individually, in modules or else altogether and are disposed in a matrix which serves for stabilization, securing, heating or cooling. A preferred embodiment of a structured reactor is that of micro reaction systems, which are also referred to in general as micro- or μ-reactors. They have the feature that at least one of the three dimensions of the reaction chamber has a measurement in the range from 1 to 2000 μm, and they thus feature a high transfer-specific inner surface area, short residence times of the reactants and high specific heat and mass transfer performances. A detailed article on this subject can be found, for example, in Jähnisch et al. in Angewandte Chemie Vol. 116, 410-451 (2004). Reference is made by way of example to European patent application EP 0903174 A1 (Bayer), in which the liquid phase oxidation of organic compounds in a microreactor consisting of an array of parallel reaction channels is described. Microreactors may additionally comprise microelectronic components as integral constituents. In contrast to known microanalytical systems, it is by no means necessary in the microreactors that all lateral dimensions of the reaction chamber are within the μm range. Instead, their dimensions are determined exclusively by the type of reaction. Accordingly, for particular reactions, useful microreactors are also those in which a particular number of microchannels is bundled, such that micro- and macrochannels or parallel operation of a multitude of microchannels may be present alongside one another. The channels are preferably arranged parallel to one another in order to enable a high throughput and to keep the pressure drop as low as possible.

Support

The supports (also referred to as "wafers") in which the structure and dimensions of the micro reaction systems are defined may be material combinations, for example silicon-silicon, glass-glass, metal-metal, metal-plastic, plastic-plastic or ceramic-ceramic, or combinations of these materials, although the preferred embodiment is a silicon-glass composite, an aluminum oxide or a zeolite. Useful supports also include polyacrylates which are produced by layer-by-layer hardening and are particularly inexpensive to produce. A further alternative is that of HAT ceramics, specifically those which are surrounded by a pressure-resistant jacket, and also all-metal reactors in which the reaction channels are coated appropriately to prevent decomposition of the oxidizing agent. A support of thickness, for example, from 100 to 2000 μm, preferably about 400 μm, is structured preferably by means of suitable microstructuring or etching techniques, for example reactive ion etching, through which it is possible, for example, to manufacture three-dimensional structures irrespective of the crystal orientation in silicon [cf. James et al. in Sci. Am. 4, 248 (1993)]. It is also possible, for example, to treat microreactors of glass in the same way. Subsequently, catalysts customary for the oxidation or alkoxylation can then be applied to the supports by suitable microstructuring techniques, for example by saturation, impregnation, precipitation from the gas phase, etc.

Supports treated in this way may have from 10 to 1000, preferably from 100 to 500 and especially from 200 to 300 micro reaction systems running parallel to one another, which may be actuated and operated either in parallel or sequentially. The geometry, i.e. the two-dimensional profile of the channels, may be very different: possible profiles include straight lines, curves, angles and the like, and combinations of these shape elements. Not all micro reaction systems need have the same geometry. The structures feature measurements of from 50 to 1500 μm, preferably from 10 to 1000 μm, and vertical walls, the depth of the channels being from 20 to 1800 μm and preferably from about 200 to 500 μm. The cross sections of each micro reaction chamber, which may but need not be square, are generally in the order of magnitude of from 20×20 to 1500×1500 μm$^2$ and especially from 100×100 to 300×300 μm$^2$, as is specified as typical, for example, by Burns et al. in Trans IChemE 77(5), 206 (1999). To supply the micro reaction chambers with the reactants, the support is etched through at the points intended for this purpose.

Finally, the structured support is bonded by a suitable process, for example anodic bonding, to a further support, for example of glass, preferably Pyrex glass, and the individual flow channels are sealed tightly to one another. Of course, depending on the substrate material, other construction and bonding techniques are also possible to realize impervious flow systems, which will be apparent to the person skilled in the art, without any need for an inventive step for this purpose.

Structuring of the Microreactors

The micro reaction systems may be divided into one or more mixing zones, one or more reaction zones, one or more mixing and reaction zones, one or more heating and cooling zones, or any combinations thereof. The microreactors preferably have three to four zones, specifically one mixing zone, one to two reaction zones and one cooling zone. The mixing zone has the task of dissolving the gaseous, but preferably liquefied, alkylene oxide in the liquid feed stream, in order to ensure that the subsequent reaction in the second zone actually proceeds exclusively in the liquid phase. In principle, it is additionally likewise possible and under some circumstances even preferred to feed the liquefied alkylene oxide into the liquid feed stream at different points in the reactor, since it is possible in this way to influence the homologous distribution of the alkoxylation product in the desired manner. In the third zone, the termination of the reaction finally takes place by lowering the temperature. It is not absolutely necessary to thermally strictly separate the first reaction zone and the second reaction zone from one another. Specifically, when the addition of a further reactant is required or several mixing points are desired instead of one, this can also take place in reaction zone 2 over and above zone 1. The micro reaction systems may be operated sequentially or else simultaneously, i.e. in parallel with defined amounts of reactant in each case and have identical or different geometries. A further possible way in which the geometry of the micro reaction systems may differ consists in the mixing angle at which the reactants meet one another and which may be between 15 and 270° and preferably from 45 to 180°. Furthermore, it is possible to cool or to heat each of the three zones independently, or to vary the temperature within one zone as desired, the reaction chambers in this example being channels whose length per zone may be from 10 to 500 mm.

In an alternative embodiment of the invention, useful structured reactors are also micro tube bundle reactors which may consist of from 10 to 100 individual capillaries with a length of from 5 to 1000 cm and a diameter of from 0.25 to 15 mm. Here too, the feedstocks are fed in through a mixing and metering apparatus in which the gaseous, but preferably liquefied, alkylene oxide is dissolved in the liquid feedstream, such that the alkoxylation takes place exclusively in the liquid phase.

The temperature of the reactors can be controlled, for example, by means of a pressurized water circuit, or by a combination of cooling water and steam circuits, thermal oil or evaporative cooling.

Alkoxylation

The alkoxylation preferably takes place in the presence of catalysts which may be of homogeneous or heterogeneous nature. In the case of use of homogeneous catalysts, it is advisable to dissolve or to disperse them in the compounds with a nucleophilic center, i.e., for example, in an alcohol, and to feed them thus to the inventive reactor; this is advisable especially in the case of the micro tube bundle reactors. Examples of suitable homogeneous catalysts include alkali metal hydroxides or alkali metal alkoxides, especially potassium hydroxide, potassium tert-butoxide and especially sodium methoxide. When heterogeneous catalysts are used, they are preferably used by coating the channels of the micro reaction systems or else as a monolithic structure or as a fixed bed. These layers then preferably have an average thickness of from 50 to 2000 and especially from 100 to 1000 nm. A preferred example of a suitable catalyst, which is applied, for example, by impregnation and subsequent calcination, is hydrotalcite. In general, the as alkylene oxides ethylene oxide and/or propylene oxide is used, where the molar ratio between the alkylene oxides and the compounds with a nucleophilic center may be from 1:1 to 200:1, preferably from 5:1 to 50:1 and especially from 8:1 to 20:1. Depending on the starting material, the reaction temperature may vary between 50 and 200° C. and is preferably from 100 to 140° C., while the pressure may be from 1 to 100 bar, preferably from 4 to 50 bar and especially from 5 to 30 bar. It should be noted that the operating pressure in the reactor is always—i.e. even at the maximum operating temperature—higher than the vapor pressure of the alkylene oxide, such that no alkylene oxide vapor phase can form and the alkoxylation actually takes place exclusively in the liquid phase.

EXAMPLES

Example 1

A technical-grade $C_{12/14}$ coconut fatty alcohol mixture (Lorol® Spezial, Cognis Deutschland GmbH & Co. KG) was preheated to 130° C. in a flow heater. A 45% by weight aqueous potassium hydroxide solution was then metered into the raw material stream, so as to establish a KOH concentration of approx. 0.1% by weight. The mixture thus obtained was freed of the water in a continuous micro falling-film reactor at a temperature of approx. 130° C. and a reduced pressure of approx. 200 mbar. Both the dried feed stream and the ethylene oxide were then compressed to a pressure of 30 bar with the aid of two pumps and metered together via a liquid distributor into a micro tube bundle reactor consisting of 50 stainless steel capillaries with a length of 25 cm and a diameter of 1 mm. The heat released in the course of addition of the ethylene oxide onto the alcohol leads to a rise in the temperature in the reactor of from 165 to 180° C. For this reason, the tube bundle reactor was cooled with a pressurized water circuit, with the aid of which it was ensured that the alkoxylation product leaving the tube bundle had only a temperature of 80° C. The heat removed by means of the cooling water circuit was utilized in order to preheat further fatty alcohol to the temperature of 130° C.

What is claimed is:

1. A process for preparing alkylene oxide addition products, comprising
   (a) providing a reactor with high internal surface area that is a micro tube bundle reactor consisting of a bundle of 10 to 100 individual capillaries with a length of 5 to 1000 cm and a diameter of 0.25 to 15 mm,
   (b) introducing alkylene oxide and compounds having a nucleophilic center into said reactor, and
   (c) reacting said alkylene oxide and said nucleophilic compounds in said reactor to form alkylene oxide addition products, wherein said alkylene oxide and said nucleophilic compounds are fed by means of a mixing and metering apparatus in which gaseous or liquefied alkylene oxide is dissolved in a liquid feed stream, such that the alkoxylation reaction takes place exclusively in the liquid phase.

2. The process of claim 1, wherein said compounds having a nucleophilic center are alcohols of the formula $R^1OH$ (I) in which $R^1$ is a linear or branched hydrocarbon moiety having from 1 to 22 carbon atoms and from 0 to 3 double bonds.

3. The process of claim 1, wherein said compounds having a nucleophilic center are carboxylic acids of the formula $R^2COOH$ (II) in which $R^2CO$ is a linear or branched acyl radical having from 1 to 22 carbon atoms and from 0 to 3 double bonds.

4. The process of claim 1, wherein said compounds with a nucleophilic center are full or partial esters of the carboxylic acids of the formula (II) with aliphatic alcohols having from 1 to 22 carbon atoms, or polyols.

5. The process of claim 4, wherein said partial esters comprise partial glycerides.

6. The process of claim 1, wherein said compounds with a nucleophilic center are amines of the formula $R^3$—NH—$R^4$ (III) in which $R^3$ and $R^4$ are each independently hydrogen, alkyl groups having from 1 to 18 carbon atoms or hydroxyalkyl groups having from 1 to 4 carbon atoms.

7. The process of claim 1, wherein the alkoxylation reaction is performed in the presence of homogeneous or heterogeneous catalysts.

8. The process of claim 7, wherein said homogeneous catalysts are dissolved or dispersed in the compounds with a nucleophilic center.

9. The process of claim 7, wherein said homogeneous catalysts are alkali metal hydroxides or alkali metal alkoxides.

10. The process of claim 7, wherein the capillaries of the micro tube bundle reactor are coated with a layer of the heterogeneous alkoxylation catalysts or designed as a monolithic structure or fixed bed.

11. The process of claim 10, wherein said catalyst layer has an average thickness of from about 50 to 2000 nm.

12. The process of claim 7, wherein said heterogeneous catalysts comprises hydrotalcites.

13. The process of claim 1, wherein said alkylene oxides are selected from the group consisting of ethylene oxide, propylene oxide and mixtures thereof.

14. The process of claim 1, wherein said alkylene oxides and said compounds with a nucleophilic center are reacted in a molar ratio of from about 1:1 to 200:1.

15. The process of claim 1, wherein the alkoxylation reaction is performed at a temperature of from about 50 to 200° C.

16. The process of claim 1, wherein the alkoxylation reaction is performed at a pressure of from about 1 to 100 bar.

17. The process of claim 1, wherein the operating pressure is always higher than the vapor pressure of the alkylene oxide.

* * * * *